(12) United States Patent
Schipper

(10) Patent No.: US 7,616,982 B1
(45) Date of Patent: Nov. 10, 2009

(54) DETERMINATION AND APPLICATION OF LOCATION AND ANGULAR ORIENTATION OF A PILL TRANSMITTER WITHIN A BODY

(75) Inventor: John F. Schipper, Palo Alto, CA (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 265 days.

(21) Appl. No.: 11/473,499

(22) Filed: Jun. 22, 2006

(51) Int. Cl.
*A61B 5/05* (2006.01)

(52) U.S. Cl. .................................. 600/424; 128/899
(58) Field of Classification Search .......... 600/109, 600/114, 160, 309, 407, 424, 476; 348/45, 348/76; 606/1, 2; 702/94–95, 150–154; 340/870.01, 901
See application file for complete search history.

(56) References Cited

U.S. PATENT DOCUMENTS

| | | | | |
|---|---|---|---|---|
| 4,494,950 A * | 1/1985 | Fischell | | 604/66 |
| 5,391,199 A * | 2/1995 | Ben-Haim | | 607/122 |
| 5,443,489 A * | 8/1995 | Ben-Haim | | 607/115 |
| 5,604,531 A * | 2/1997 | Iddan et al. | | 348/76 |
| 6,044,297 A * | 3/2000 | Sheldon et al. | | 607/17 |
| 6,239,724 B1 * | 5/2001 | Doron et al. | | 340/870.28 |
| 6,240,312 B1 * | 5/2001 | Alfano et al. | | 600/476 |
| 6,361,507 B1 * | 3/2002 | Foxlin | | 600/595 |
| 6,800,060 B2 * | 10/2004 | Marshall | | 600/309 |
| 6,934,573 B1 * | 8/2005 | Glukhovsky et al. | | 600/407 |
| 6,950,690 B1 * | 9/2005 | Meron et al. | | 600/424 |
| 6,958,034 B2 * | 10/2005 | Iddan | | 600/114 |
| 6,984,205 B2 * | 1/2006 | Gazdzinski | | 600/160 |
| 7,001,329 B2 * | 2/2006 | Kobayashi et al. | | 600/114 |
| 7,009,561 B2 * | 3/2006 | Menache et al. | | 342/463 |
| 7,009,634 B2 * | 3/2006 | Iddan et al. | | 348/76 |
| 7,023,380 B2 * | 4/2006 | Schneider | | 342/361 |
| 7,039,453 B2 * | 5/2006 | Mullick et al. | | 600/476 |
| 7,116,352 B2 * | 10/2006 | Yaron | | 348/45 |
| 7,118,529 B2 * | 10/2006 | Glukhovsky et al. | | 600/160 |
| 7,149,584 B1 * | 12/2006 | Koh et al. | | 607/60 |
| 7,160,258 B2 * | 1/2007 | Imran et al. | | 600/593 |
| 7,295,877 B2 * | 11/2007 | Govari | | 607/60 |
| 7,395,181 B2 * | 7/2008 | Foxlin | | 702/155 |
| 2002/0065455 A1 * | 5/2002 | Ben-Haim et al. | | 600/407 |
| 2002/0173718 A1 * | 11/2002 | Frisch et al. | | 600/424 |
| 2003/0191568 A1 * | 10/2003 | Breed | | 701/36 |
| 2003/0216639 A1 * | 11/2003 | Gilboa et al. | | 600/424 |
| 2004/0138555 A1 * | 7/2004 | Krag et al. | | 600/424 |

(Continued)

*Primary Examiner*—Long V Le
*Assistant Examiner*—Salieu M Abraham
(74) *Attorney, Agent, or Firm*—John F. Schipper; Robert M. Padilla

(57) ABSTRACT

A mobile pill transmitter system that moves through or adjacent to one or more organs in an animal's body and that provides signals from which the pill's present location and/or present angular orientation can be determined. The system also provides signals from which the present roll angle of the pill, about a selected axis, can be determined. When the location coordinates and the roll angle of the pill are within selected ranges, an aperture on the pill container releases a selected chemical into or onto the body. Optionally, the pill as it moves also provides a sequence of visually perceptible images; the times for image formation may correspond to times at which the pill transmitter system location or image satisfies one or at least four different criteria.

11 Claims, 3 Drawing Sheets

U.S. PATENT DOCUMENTS

| | | | |
|---|---|---|---|
| 2005/0027330 A1* | 2/2005 | Govari | 607/60 |
| 2005/0033142 A1* | 2/2005 | Madden et al. | 600/407 |
| 2006/0262008 A1* | 11/2006 | Sanyal | 342/120 |
| 2007/0106717 A1* | 5/2007 | Dundar et al. | 708/204 |
| 2007/0156123 A1* | 7/2007 | Moll et al. | 606/1 |
| 2007/0197896 A1* | 8/2007 | Moll et al. | 600/407 |
| 2007/0225550 A1* | 9/2007 | Gattani et al. | 600/101 |
| 2008/0176681 A1* | 7/2008 | Donahoe | 473/570 |
| 2009/0084173 A1* | 4/2009 | Gudat et al. | 73/146 |
| 2009/0118610 A1* | 5/2009 | Karmarkar et al. | 600/420 |

* cited by examiner

DETERMINATION AND APPLICATION OF LOCATION AND ANGULAR ORIENTATION OF A PILL TRANSMITTER WITHIN A BODY

ORIGIN OF THE INVENTION

This invention was made by an employee of the U.S. government. The U.S. government has the right to make, use and/or sell the invention described herein without payment of compensation, including but not limited to payment of royalties.

FIELD OF THE INVENTION

This invention relates to determination of location and angular orientation of a signal transmitting mobile device within a human or other animal body.

BACKGROUND OF THE INVENTION

Medical imaging procedures now include, in some circumstances, provision of a sequence of images, in video format, of the interior of an organ through which the imaging mechanism passes. The images provided are often life-like and contain considerable detail. However, as yet no such imaging mechanism has provided, at the same time, location coordinates and/or angular orientation coordinates, associated with this mechanism, indicating where the mechanism is presently located and/or presently oriented, when a particular image is made. This location and/or orientation information would be useful in associating a location and/or orientation with a particular image where a troublesome or pathological organ condition is indicated by the image. This location and/or orientation information would also be useful in determining, on a first pass or on a second pass, a location and/or orientation where a particular medical treatment or pharmaceutical is to be delivered to the organ or a visibly perceptible image is to be made.

What is needed is a method and system for determining location and angular orientation, exact and without iterations or approximations, of a mobile signal transmitting device, moving within a human or other animal body ("user") at each of a sequence of times. Preferably, the system should consume minimal additional energy and should permit arbitrary separation of consecutive times in the time sequence(s). Preferably, the system should flexible to permit changes in the parameters to be monitored or examined. Preferably, the system should permit accurate determination of one or more times and corresponding locations for delivery of a drug or other chemical substance to the user.

SUMMARY OF THE INVENTION

These needs are met by the invention, which provides and applies an algorithm for exact determination of location coordinates and angular orientation coordinates for a mobile pill transmitter ("PT") or other similar device that is introduced into and moves within a human or other animal body. A set of as many as eight nonlinear equations is developed and applied, relating propagation of a wireless signal between either of two, three or more or more transmitting antennas located on the PT to four or more non-coplanar receiving antennas located on a signal receiver appliance worn by the user. The equations are solved exactly, without approximations or iterations, and are applied in several environments: (1) association of a visual image, transmitted by the PT at each of a second sequence of times, with a PT location and PT angular orientation at that time; (2) determination of a position within the body at which a drug or chemical substance or other treatment is to be delivered to a selected portion of the body; (3) monitoring, after delivery, of the effect(s) of administration of the treatment; and (4) determination of one or more positions within the body where provision and examination of a finer scale image is warranted.

The invention is applicable wherever a mobile pill transmitter is administered and followed within an organ of a human or other animal body. Provision of location and angular orientation coordinates can be used wherever examination and/or therapeutic treatment and/or post-treatment examination of the user is required.

DESCRIPTION OF BEST MODES OF THE INVENTION

Figure 1:
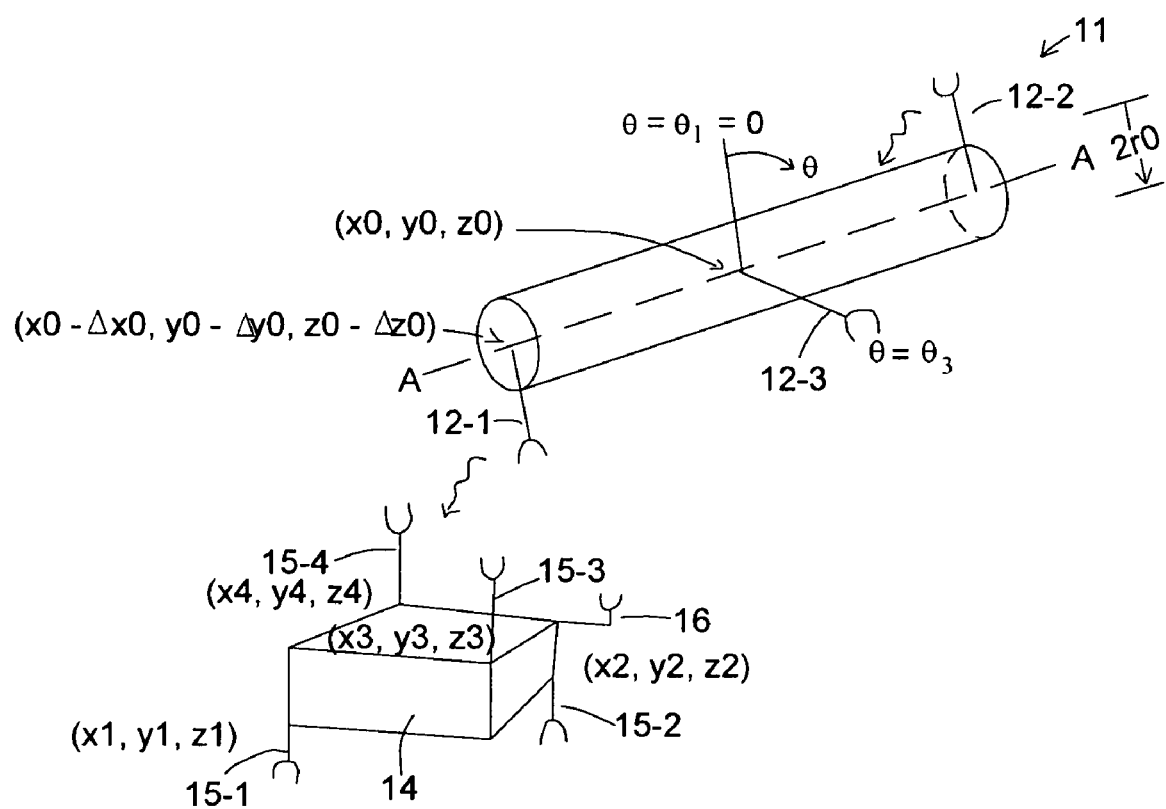
FIG. 1 schematically illustrates relationships of a mobile pill transmitter and a signal receiving appliance operated according to embodiments of the invention.

With reference to FIG. 1, a mobile pill transmitter ("PT") 11 is introduced into the body of a human or other animal ("user"), and the PT moves slowly within or adjacent to a body organ, for example, the stomach, small intestine, large intestine or other organ in the GI tract. First and second signal transmitters, 12-$i$ ($i$=1, 2), are provided at spaced apart locations on the PT 11 with location coordinates (x0±a·Δx0, y0±a·Δy0, z0±a·Δz0), where (x0,y0,z0) are the location coordinates of a specified center of the PT and a (0<a≦1) is a selected real number (e.g., a=0.5 or a=1). Herein, it is assumed that a=1, although any other permitted choice can be used. The pill transmitter 11 is introduced into, and travels through a portion of, the user's body to form and transmit visual images and/or other electronic signals, using a data antenna 13 that may coincide with, or be different from, one of the antennas 12-$i$ ($i$=1,2).

A signal receiving appliance 14, spaced apart from the P[1], is provided with first, second, third and fourth spaced apart, signal receiving antennas, 15-$j$ ($j$=1, 2, 3, 4), which are non-coplanar so that the four antenna locations do not lie on a single plane. The first, second, third and fourth antennas have the respective location coordinates (x1,y1,z1), (x2,y2,z2), (x3,y3,z3) and (x4,y4,z4). The appliance 14 has one or more data-receiving antennas 16, which may be different from, or may coincide with, one or more of the four signal receiving antennas 15-$j$, to receive the data signals from the data antenna(s) 13.

A location signal, transmitted from the transmitter antenna 12-$i$ and received by the receiver antenna 15-$j$, will require a signal propagation time Δt($i$,$j$) determined by the relation $$(xj-x0\pm\Delta x0)^2+(yj-y0\pm\Delta y0)^2+(zj-z0\pm\Delta z0)^2=\{c'\Delta t(i,j)\}^2, \quad (1\text{-}i\text{-}j)$$

where, for example, +Δx0 and −Δx0 correspond to $i$=1 and $i$=2, respectively, c' is a representative velocity of signal propagation within the body, and Δt($i$,$j$) is signal propagation time (measured or estimated) from transmitter no. $i$ to receiver no. $j$. Squaring Eqs. (1-1-j) and (1-2-j) and forming the difference yields a new sequence of relations:

$$4(xj-x0)\Delta x0+4(yj-y0)\Delta y0+4(zj-z0)\Delta z0=c'^2\{\Delta t(1,j)^2-\Delta t(2,j)^2\} \quad (2\text{-}j)$$

Subtracting Eq. (2-1) from Eq. (2-2), Eq. (2-1) from Eq. (2-3) and Eq (2-1) from Eq. (2-4) provides three independent relations, which are expressed in matrix form:

$$M \begin{vmatrix} \Delta x0 \\ \Delta y0 \\ \Delta z0 \end{vmatrix} = (c^2/4) \begin{vmatrix} \{\Delta t(1,2)^2 - \Delta t(2,2)^2 - \Delta t(1,1)^2 + \Delta t(2,1)^2\} \\ \{\Delta t(1,3)^2 - \Delta t(3,3)^2 - \Delta t(1,1)^2 + \Delta t(3,1)^2\} \\ \{\Delta t(1,4)^2 - \Delta t(4,4)^2 - \Delta t(1,1)^2 + \Delta t(4,1)^2\} \end{vmatrix} \quad (3)$$

$$\begin{vmatrix} \Delta x0 \\ \Delta y0 \\ \Delta z0 \end{vmatrix} = (c^2/4) M^{-1} \begin{vmatrix} \{\Delta t(1,1)^2 - \Delta t(2,1)^2 - \Delta t(1,2)^2 + \Delta t(2,2)^2\} \\ \{\Delta t(1,1)^2 - \Delta t(3,1)^2 - \Delta t(1,3)^2 + \Delta t(3,3)^2\} \\ \{\Delta t(1,1)^2 - \Delta t(4,1)^2 - \Delta t(1,4)^2 + \Delta t(4,4)^2\} \end{vmatrix} \quad (4)$$

$$M = \begin{vmatrix} x2 - x1 & y2 - y1 & z2 - z1 \\ x3 - x1 & y3 - y1 & z3 - z1 \\ x4 - x1 & y4 - y1 & z4 - z1 \end{vmatrix}. \quad (5)$$

The precision matrix M has a non-zero determinant, because the four locations with coordinates are non-coplanar. Thus, Eq. (3) has a unique solution vector $\{\Delta x0 \, \Delta y0, \, \Delta z0\}^{tr}$. The square of the separation distance d between the two transmitting antenna locations is $$4\{\Delta x0^2 + \Delta y0^2 + \Delta z0^2\} = d^2, \quad (6)$$

where d is a known, controllable physical distance. Equation (6) serves as a consistency relation to evaluate the accuracy of Eq. (4).

One can also add Eq. (1-1-i) to Eq. (1-2-j) and use Eq. (6) to obtain $$(xj - x0)^2 + (yj - y0)^2 + (zj - z0)^2 + d^2/4, \quad (7\text{-}j)$$
$$= c^2 \{\Delta t(1, j)^2 + \Delta t(2, j)^2\}/2 \, (j = 1, 2, 3, 4)$$

and observe that $$xj - x0 = (xj - x1) + (x1 - x0)(j=1, 2, 3, 4). \quad (8\text{-}j)$$

Using Eqs. (8-j), Eqs. (7-j) (j=2, 3, 4) can be re-expressed as $$(x1 - x0)^2 + 2(x1 - x0)(xj - x1) + (xj - x1)^2 + \quad (9\text{-}j)$$
$$(y1 - y0)^2 + 2(y1 - y0)(yj - y1) + (yj - y1)^2 +$$
$$(z1 - z0)^2 + 2(z1 - z0)(zj - z1) + (zj - z1)^2 + d^2/4 =$$
$$c^2 \{\Delta t(1, j)^2 + \Delta t(2, j)^2\}/2.$$

Subtracting Eq. (9-1) from Eq. (9-j), for each of j=2, 3, 4, yields three linear relations in the remaining unknowns (j=2, 3, 4):

$$(x1 - x0)(xj - x1) + (y1 - y0)(yj - y1) + (z1 - z0)(zj - z1) = \quad (10\text{-}j)$$
$$c^2 \{\Delta t(1, 2)^2 + \Delta t(2, 2)^2\} - \Delta t(1, 1)^2 - \Delta t(2, 1)^2\}$$

$$M \begin{vmatrix} x1 - x0 \\ y1 - y0 \\ z1 - z0 \end{vmatrix} = c^2 \begin{vmatrix} \{\Delta t(1,2)^2 - \Delta t(2,2)^2 - \Delta t(1,1)^2 + \Delta t(2,1)^2\} \\ \{\Delta t(1,3)^2 - \Delta t(3,3)^2 - \Delta t(1,1)^2 + \Delta t(3,1)^2\} \\ \{\Delta t(1,4)^2 - \Delta t(4,4)^2 - \Delta t(1,1)^2 + \Delta t(4,1)^2\} \end{vmatrix} \quad (11)$$

$$\begin{vmatrix} x1 - x0 \\ y1 - y0 \\ z1 - z0 \end{vmatrix} = c^2 M^{-1} \begin{vmatrix} \{\Delta t(1,2)^2 - \Delta t(2,2)^2 - \Delta t(1,1)^2 + \Delta t(2,1)^2\} \\ \{\Delta t(1,3)^2 - \Delta t(3,3)^2 - \Delta t(1,1)^2 + \Delta t(3,1)^2\} \\ \{\Delta t(1,4)^2 - \Delta t(4,4)^2 - \Delta t(1,1)^2 + \Delta t(4,1)^2\} \end{vmatrix} \quad (12)$$

The location coordinates (x0,y0,z0) of the center are then obtained by subtracting the known values of the antenna coordinates (x1,y1,z1) in Eqs. (12).

Note that inversion of the precision matrix M is involved in each of the solution component triples $\{\Delta x0 \, \Delta y0, \, \Delta z0\}^{tr}$ and $\{x0,y0,z0\}^{tr}$. The quantity $S=\{\det(M)\}^{-1}$ is a measure of the sensitivity of these solutions to small errors in measurement and/or timing, which may arise from signal-to-noise problems, from signal propagation problems, from location measurement errors and/or from timing errors. The sensitivity varies approximately monotonically with S, with S=0 being most desirable, so that, as the four receiver antenna locations approach a common plane (coplanar configuration), the sensitivity approaches an infinite value. For this reason, it is preferable to choose the location coordinates, (x1,y1,z1), (x2,y2,z2), (x3,y3,z3) and (x4,y4,z4), for the four receiver antennas to maximize the value det(M)=1/S, consistent with the constraints imposed on the coordinates.

The solutions of Eqs. (3) and (11) provide a determination of the location coordinates (x0,y0,z0) for the center of the PT device 11 and of the angular orientation ($\Delta x0,\Delta y0,\Delta z0$) of this device relative to axes of a Cartesian coordinate system, which may include pitch and yaw angles of the device.

Another quantity, roll angle $\theta$ of the device about its longitudinal axis AA, illustrated in FIG. 1, may be needed in some applications. To determine $\theta$, it is convenient to provide a third signal transmitting antenna 12-3 on the PT, at a location that is not collinear with the locations of the other two signal transmitting antennas, 12-1 and 12-2.

If, as is likely, the PT is cylindrical and the roll angle $\theta$ is to be estimated, it is preferable to locate the two transmitting antennas, 12-1 and 12-2, at antipodal locations on the cylinder, as illustrated in FIG. 1. With this configuration, the line L(1,2) connecting the two transmitting antennas, 12-1 and 12-2, is now oriented at an angle $$\Phi = \tan^{-1}\{r0/\{\Delta x0^2 + \Delta y0^2 + \Delta z0^2\}^{1/2}\}, \quad (13)$$

relative to the axis AA, Where r0 is the radius of the cylinder. The third transmitting antenna 12-3 is assumed to be located at a known, selected rotational angle $\theta=\theta3$ (e.g., $15° \leq \theta3 \leq 90°$) relative to a longitudinal plane $\Pi$ (defined by roll angle $\theta=0$) that contains the transmitting antennas 12-1 and 12-2.

Where the cylinder or PT 11 has rolled or rotated by an angle $\theta$ relative to its reference position ($\theta=0$), the distance $\Delta r(i,j)$ from the first and second transmitting antennas 12-$i$ ($i=1, 2$) to the receiving antenna 15-$j$ is related to the elapsed time $\Delta t(i,j)$ for the signal propagation by $$\Delta r(i, j)^2 = \{xj - x0 - r0 \cdot \cos(\theta - \theta3)\}^2 + \quad (13\text{-}i\text{-}j)$$
$$\{yj - y0 - r0 \cdot \sin(\theta - \theta3)\}^2 + \{zj - z0 + \Lambda z0\}^2, \, = c^2 \Delta t(i, j)^2,$$

and the distance from the third transmitting antenna 12-3 to the receiving antenna 15-$j$ is related to the elapsed time $\Delta t(3,j)$ for the signal propagation by $$\Delta r(3, j)2 = \{xj - x0 - r0 \cdot \cos(\theta)\}^2 + \qquad (13\text{-}3\text{-}j)$$
$$\{yj - y0 - r0 \cdot \sin(\theta)\}^2 + \{zj - z0\}^2, \ = c^2 \Delta t(3, j)^2,$$

where the terms $+\Delta z0$ and $-\Delta z0$ in Eq. (13-j) correspond to i=1 and i=2, respectively.

The difference in distance squared $\Delta r^2$ between Eq. (13-i-j) and (13-3-j) becomes $$\Delta r(i,3,j)^2 - \Delta r(3,j)^2 = \pm 2(zi-z0)\Delta z0 + \Delta z0^2 - 2r0(xi-x0)\{\cos(\theta-\theta3)-\cos\theta\} - 2r0(yi-y0)\{\sin(\theta-\theta3)-\sin\theta\} = c^2\{\Delta t(i,j)^2 - \Delta t(3,j)^2\}. \qquad (14)$$

Using multiple angle trigonometric identities, one verifies the relations $$\cos(\theta - \theta3) - \cos\theta = \qquad (15)$$
$$\cos\theta\{\cos\theta3 - 1\} + \sin\theta \cdot \sin\theta3 = \{2(1 - \cos\theta3)\}^{1/2}\cos\{\theta - \psi3\},$$

$$\sin(\theta - \theta3) - \sin\theta = \qquad (16)$$
$$\sin\theta\{\cos\theta3 - 1\} + \cos\theta \cdot \sin\theta3 = \{2(1 - \cos\theta3)\}^{1/2}\sin\{\theta - \psi3\},$$

$$\psi3 = \tan^{-1}\{\sin\theta3/(\cos\theta3 - 1)\} = (\theta3 - \pi)/2 \qquad (17)$$

Equation (14) can be rewritten as $$\Delta r(i, j)^2 - \Delta r(3, j)^2 = \qquad (18)$$
$$\pm 2(zi - z0)\Delta z + \Delta z^2 - 2r0\{(xi - x0)^2 + (yi - y0)^2\}^{1/2}$$
$$\{2(1 - \cos\theta3)\}^{1/2}\cos\{\theta - \psi3 - \psi\} = c^2\{\Delta t(i, j)^2 - \Delta t(3, j)^2\},$$

$$\psi = \tan^{-1}\{(yi - y0)/(xi - x0)\}. \qquad (19)$$

All quantities in Eq. (18) are known except the roll angle $\theta$, which will vary as the PT 11 moves along a path in or adjacent to an organ in the body. The quantity $\theta-\psi3-\psi$ in Eq. (18) can be estimated to within a multiplicative factor ($\pm 1$) by measurement of the propagation time difference $\Delta r(i,j)^2 - \Delta r(3,j)^2$.

A dispensing aperture for a chemical (pharmaceutical or other substance), can be initially located at the initial rotational angle $\theta=0$, can be allowed to move rotationally with the roll angle $\theta$, and can be caused to dispense the chemical when the aperture is located adjacent to, and is directed at, a target section of an organ that is to be treated, at a target roll angle value. Given a knowledge of the roll angle $\theta$ and of the location (x0,y0,z0) of the center of the PT 11, the chemical dispensation point is easily estimated.

Optionally, the PT 11 also forms and transmits signals representing visually perceptible images at a sequence of times as the pill moves through the body, using the signal receiving antenna 16. In a first option, the antenna 16 is part of a signal transceiver that (1A) determines when location coordinates of the pill lie within selected ranges, such as $$(xf1 \leq x0(t) \leq xf2, yf1 \leq y0(t) \leq yf2, zf1 \leq z0(t) \leq zf2), \qquad (20)$$

and (1B) when the pill location coordinates lie within these ranges, a signal is transmitted at the transceiver that causes the pill transmitter system to form and transmit a visually perceptible image. In a second option, the PT forms and transmits an image at two consecutive image transmission times, $t_1$ and $t_2$, when $$\{(x0(t_2)-x0(t_1))^2 + (y0(t_2)-y0(t_1))^2 + (z0(t_2)-z0(t_1))^2\}^{1/2} \geq \Delta r(\text{thr}), \qquad (21)$$

where $\Delta r$ is a selected threshold distance. In a third option, the PT forms and transmits an image at each of a selected sequence of times $\{t_n\}_n$, where $$|t_{n+1}-t_n| \geq \Delta t(\text{thr}), \qquad (22)$$

and $\Delta t(\text{thr})$ is a selected separation time. In a fourth option, a numerical measure of image difference $ID(t_1;t_2)$ is provided between an image formed at each of two times, $t_1$ and $t_2$ ($>t_1$), and the image $I(t_2)$ is transmitted when $$|ID(t1;t2)| \geq \Delta I(\text{thr}), \qquad (23)$$

where $\Delta I(\text{thr})$ is a selected image difference threshold. Each of these image transmission options is made possible by availability of the location coordinates (x0(t),y0(t),z0(t)), or a related quantity.

Figure 2A:
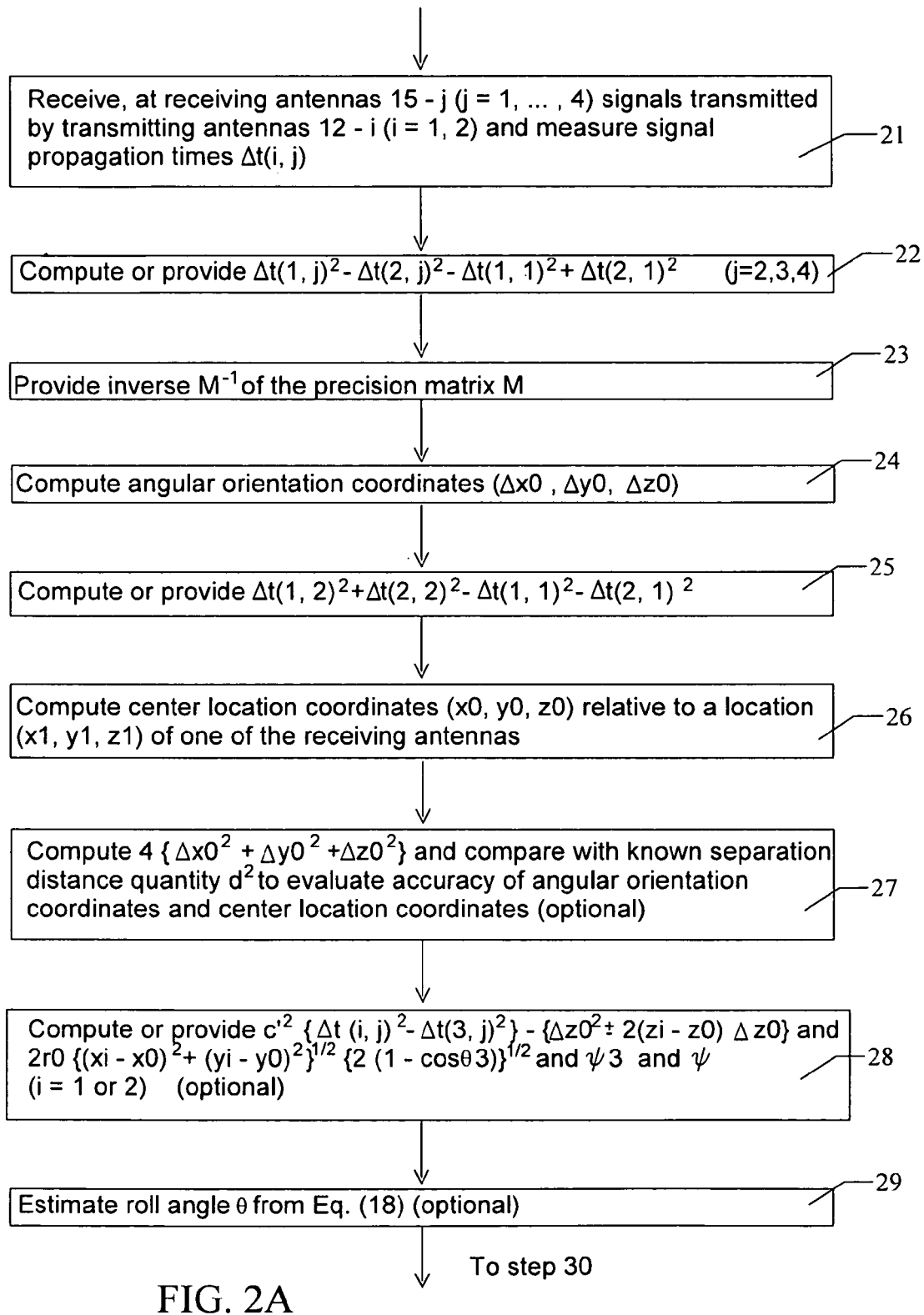
FIGS. 2A/2B are a flow chart of procedures for practicing the invention.
Figure 2B:
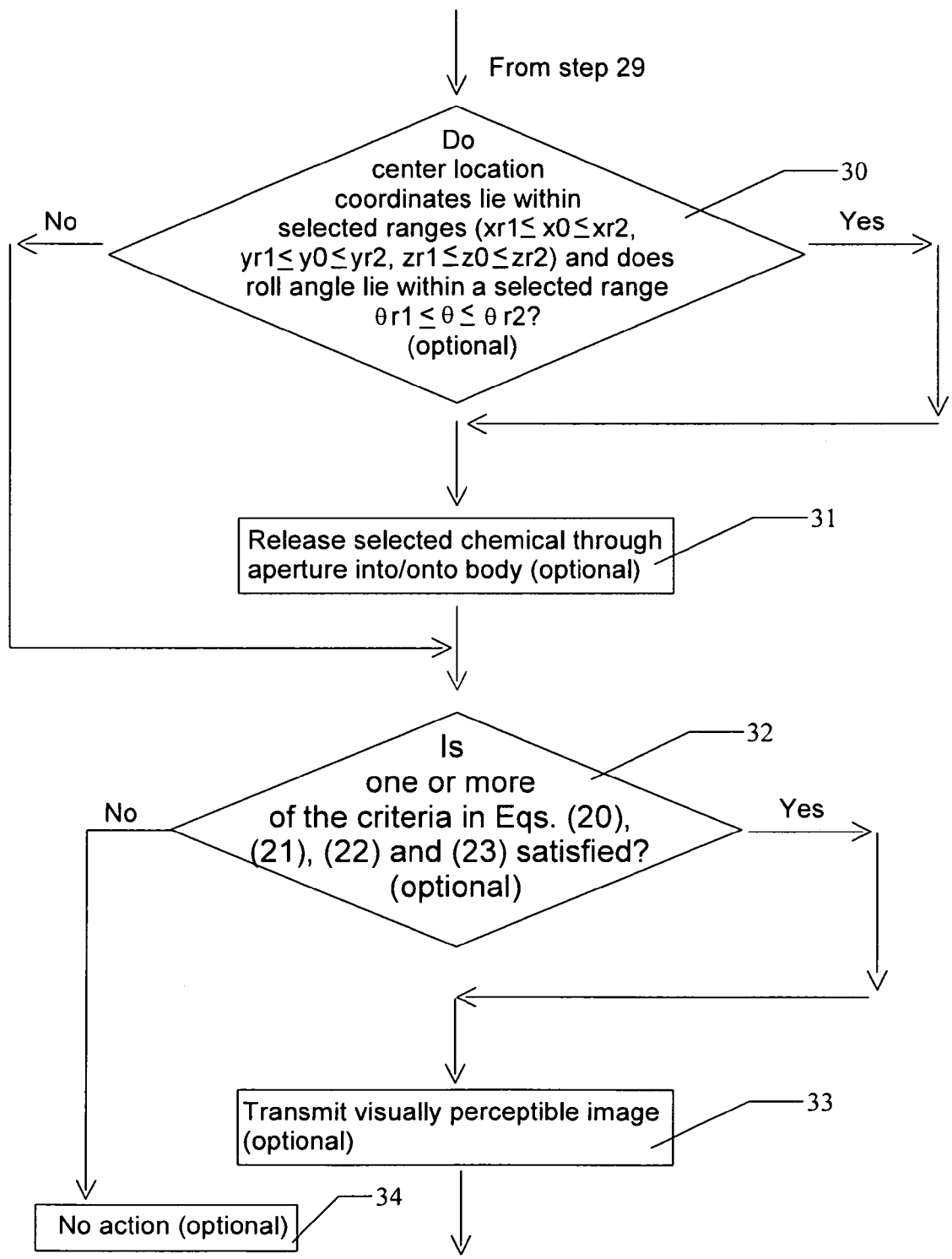

FIG. 2 is a flow chart covering procedures for practicing the invention. In step 21, the system receives, at the receiving antennas 15-$j$ (j=1, 2, 3, 4 in FIG. 1), signals transmitted by the transmitting antennas 12-$i$ (i=1, 2) and measures the signal propagation times $\Delta t(i,j)$ from transmitter no. i to receiver no. j. Each transmitter may transmit a signal having a different frequency, indicium or other signal signature, or the two sets of signals (i=1, 2) may be transmitted in different, non-overlapping times intervals, with temporal separations $\Delta t(\text{sep})=0.001-5$ sec, or more if desired. In steps 22 and 23, the system respectively computes or otherwise provides the quantities $(c'^2/4)\{\Delta t(1,j)^2 - \Delta t(2,j)^2 - \Delta t(1,1)^2 + \Delta t(2,1)^2\}$ (j=2, 3, 4) and the entries of the matrix $M^{-1}$, where M is the precision matrix, set forth in Eq. (5). In step 24, the system computes the angular orientation coordinates ($\Delta x0, \Delta y0, \Delta z0$) as set forth in Eq. (4), where c' is a measured or estimated velocity of signal propagation within and adjacent to the body.

In step 25, the PT system computes or otherwise provides the quantities $c'^2\{\Delta t(1,2)^2 + \Delta t(2,2)^2 - \Delta t(1,1)^2 - \Delta t(2,1)^2\}$. In step 26, the PT system computes the center location coordinates (x0,y0,z0) of the PT relative to a location (x1,y1,z1) of one of the receiving antennas, as set forth in Eq. (12). From these values, one can determine the center location and angular orientation of the PT, relative to a Cartesian or other coordinate system and relative to the location (x1,y1,z1) of one of the receiving antennas. In step 27 (optional), the system computes the square of the transmitting antenna separation distance, $4\{\Delta x0^2+\Delta y0^2+\Delta z0^2\}$, and compares this with the square of the known separation distance $d^2$, to evaluate the accuracy of the determinations in one or more of the steps 21-25.

In step 28 (optional), $c'^2\{\Delta t(i,j)^2 - \Delta t(3,j)^2\} - \{\Delta z0^2 \pm 2(zi-z0)\Delta z0\}$, $2r0\{(xi-x0)^2+(yi-y0)^2\}^{1/2}\{2(1-\cos\theta3)\}^{1/2}$, $\psi3$ and $\psi$ are computed or otherwise provided for at least one of i=1 or 2. In step 29 (optional), the relation $$2r0\{(xi-x0)^2+(yi-y0)^2\}^{1/2}\{2(1-\cos\theta3)\}^{1/2}\cos\{\theta-\psi3-\psi\} = \qquad (18)$$
$$-c'^2\{\Delta t(i,j)^2 - \Delta t(3,j)^2\} + \{\Delta z0^2 \pm 2(zi-z0)\Delta z0\}$$

from Eq. (18) is used to estimate the quantities $\cos\{\theta-\psi3-\psi\}$ and the roll angle $\theta$, where $\theta3$, $\psi3$ and $\psi$ are quantities discussed in the preceding. In step 30 (optional), the system determines if the center location coordinates (x0,y0,z0) lie within selected ranges (xr1≤x0≤xr2, yr1≤y0≤yr2, zr1≤z0≤zrs) and/or the roll angle $\theta$ lies in a selected range ($\theta r1 \leq \theta \leq \theta r2$) so that a selected chemical can be released through the aperture into or onto the body. If the answer to the query in step 30 is "yes," the PT system releases the selected chemical, in step 31 (optional). If the answer to the query in step 30 is "no,", the system moves to the next step, if any.

In step 32 (optional), the PT system determines if one (or more than one) of the selected criteria set forth in Eqs. (20), (21), (22) and (23) is satisfied. If the answer to the query in step 32 is "yes," the PT system forms and transmits a visually perceptible image, in step 32 (optional). If the answer to the query in step 32 is "no," the system takes no further action at that time, in step 34 (optional).

The invention thus provides: (1) location coordinates and/or angular orientation coordinates for the PT, as a function of time; (2) an estimation of roll angle for the PT, as a function of time; (3) an estimation of one or more times a selected chemical is appropriately delivered to an organ; and (4) determination of a sequence of times for formation and transmission of a signal representing an image sensed by the PT.

What is claimed is:

1. A method for determination of at least one location coordinate and at least one angular orientation coordinate of a mobile device that moves within or adjacent to at least one organ in a human or other animal body, the method comprising:

(1) providing first and second spaced apart signal transmitting antennas, having index values i=1 and i=2, respectively, on the device, spaced apart along a selected axis of the device, and transmitting a first sequence and a second sequence of distinguishable signals at the first and second transmitting antennas, respectively, where the first and second transmitting antennas have location coordinates $(x0+\Delta x0, y0+\Delta y0, z0+\Delta z0)$ and $(x0-\Delta x0, y0-\Delta y0, z0-\Delta z0)$, respectively, a central location of the mobile device has location coordinates $(x0,y0,z0)$, and the coordinate values $x0, y0, z0, \Delta x0, \Delta y0, \Delta z0$ are to be determined, and $(x,y,z)$ are location coordinates in a selected Cartesian coordinate system;

(2) receiving the first and second sequences of transmitted signals at least first, second, third and fourth spaced apart, non-coplanar signal receiving antennas, having index values j=1, 2, 3, 4, respectively, having substantially fixed and known location coordinates $(xj,yj,zj)$, and being located adjacent to the body;

(3) for each transmitted signal in each of the first and second sequences, providing an elapsed time of signal propagation $\Delta t(i,j)$ between the first transmitting antenna (i=1) or second transmitting antenna (i=2) and the first, second, third or fourth signal receiving antenna (j=1, 2, 3, 4, respectively), where $\Delta t(i,j)$ is expressed by a relation $$c'^2 \Delta t(i=1,j)^2 = (xj-x0+\Delta x0)^2+(yj-y0+\Delta y0)^2+(zj-z0+\Delta z0)^2,$$

$$c'^2 \Delta t(i=2,j)^2 = (xj-x0-\Delta x0)^2+(yj-y0-\Delta y0)^2+(zj-z0-\Delta z0)^2,$$

where $c'$ is a representative value of propagation of a transmitted electromagnetic signal within the body;

(4) estimating the values $\Delta x0, \Delta y0, \Delta z0, x0, y0$ and $z0$ by the relations $$\begin{bmatrix} \Delta x0 \\ \Delta y0 \\ \Delta z0 \end{bmatrix} = (c'^2/4)M^{-1} \begin{bmatrix} \{\Delta t(1,1)^2 - \Delta t(2,1)^2 - \Delta t(1,2)^2 + \Delta t(2,2)^2\} \\ \{\Delta t(1,1)^2 - \Delta t(3,1)^2 - \Delta t(1,3)^2 + \Delta t(3,3)^2\} \\ \{\Delta t(1,1)^2 - \Delta t(4,1)^2 - \Delta t(1,4)^2 + \Delta t(4,4)^2\} \end{bmatrix},$$

$$\begin{bmatrix} x1-x0 \\ y1-y0 \\ z1-z0 \end{bmatrix} = (c'^2/4)M^{-1} \begin{bmatrix} \{\Delta t(1,2)^2 - \Delta t(2,2)^2 - \Delta t(1,1)^2 + \Delta t(2,1)^2\} \\ \{\Delta t(1,3)^2 - \Delta t(3,3)^2 - \Delta t(1,1)^2 + \Delta t(3,1)^2\} \\ \{\Delta t(1,4)^2 - \Delta t(4,4)^2 - \Delta t(1,1)^2 + \Delta t(4,1)^2\} \end{bmatrix},$$

$$M = \begin{bmatrix} x2-x1 & y2-y1 & z2-z1 \\ x3-x1 & y3-y1 & z3-z1 \\ x4-x1 & y4-y1 & z4-z1 \end{bmatrix};$$

(5) interpreting the quantities $(x1-x0, y1-y0, z1-z0)$ as location coordinates of the mobile device central location relative to location coordinates $(x1,y1,z1)$ of the first receiving antenna; and (6) when $D=\{(\Delta x0)^2+(\Delta y0)^2+(\Delta z0)^2\}^{1/2}$, is non-zero, interpreting the quantities $(\Delta x0/D, \Delta y0/D, \Delta z0/D)$, where as direction cosines with respect to x-, y- and z-Cartesian coordinate axes, corresponding to angular orientation of a line segment along the selected axis.

2. The method of claim 1, further comprising evaluating accuracy of said angular orientation components by comparing a sum of squares of said angular orientation components, $4\{\Delta x0^2+\Delta y0^2+\Delta z0^2\}$, with a square $d^2$ of a known distance between two selected locations on said mobile device.

3. The method of claim 1, further comprising estimating a roll angle $\theta$ of said mobile device about a selected axis by a process comprising:

selecting a location on said mobile device corresponding to a roll angle value, $\theta=\theta 3$, about a selected axis for said mobile device;

providing a third signal transmitting antenna, numbered i=3, on said mobile device at a location selected with reference to the roll angle value $\theta=\theta 3$;

providing a square $\Delta t(3,j)^2$ of elapsed time of signal propagation between the third signal transmitting antenna and at least one of said signal receiving antenna, numbered j, providing a first selected angle value $\psi=(\theta 3-\pi)/2$ and a second selected angle value $\psi$;

providing a value $\Delta z0$ for said angular orientation component and values, $xi-x0, yi-y0$ and $zi-z0$, relating said location coordinate $(x0,y0,z0)$ to corresponding location coordinate $(xi,yi,zi)$ (I=1 or 2) of said signal receiving antenna; and estimating a roll angle $\theta$ of said mobile device at least one time from a relation $$2r0\{(xi-x0)^2+(yi-y0)^2\}^{1/2}\{2(1-\cos\theta 3)\}^{1/2}\cos\{\theta 3-\psi 3-\psi\} = -c'^2\{\Delta t(i,j)^2 - \Delta t(3,j)^2\} + \{\Delta z0^2 \pm 2(zi-z0)\Delta z0\},$$

where $r\theta$ is a radius of said mobile device, measured in a direction substantially perpendicular to the selected axis for said mobile device.

4. The method of claim 3, further comprising choosing said angle $\psi$ to be $\psi=\tan^{-1}\{(yi-y0)/(xi-x0)\}$.

5. The method of claim 3, further comprising:

providing said mobile device with a controllable aperture and with a source of a selected chemical associated with the aperture;

estimating a time when (1) said location coordinates $(x0, y0,z0)$ for said mobile device lie in selected ranges $(xr1 \leq x0 \leq xr2, yr1 \leq y0 \leq yr2, zr1 \leq z0 \leq zr2)$ and (2) said roll angle $\theta$ lies within a selected range, $\theta r1 \leq \theta \leq \theta r2$; and when the conditions (1) and (2) are satisfied, causing said mobile device to release the selected chemical through the aperture.

6. The method of claim 1, further comprising:

causing said mobile device to form and transmit signals representing visually perceptible images at a sequence of two or more image formation times, when a selected criterion is satisfied.

7. The method of claim 6, further comprising choosing said selected criterion to comprise: each image formation time corresponds to a time, $t=t_f$, at which said location coordinates $(X0(t_f), y0(t_f), z0(t_f))$ lie within one or more selected ranges $(xf1 \leq x0 \leq xf2, yf1 \leq y0 \leq yf2, zf1 \leq z0 \leq zf2)$.

8. The method of claim 6, further comprising choosing said criterion to comprise: two consecutive image formation times, $t=t_{f1}$ and $t=t_{f2}$, correspond to locations $(x0(t_f), y0(t_f), z0(t_f))$ of said mobile device that satisfy $$\{(x0(t_{f2})-x0(t_{f1}))^2+(y0(t_{f2})-y0(t_{f1}))^2+(z0(t_{f2})-z0(t_{f2}))^2\}^{1/2} \geq \Delta r(\text{thr}),$$

where $\Delta r(\text{thr})$ is a selected threshold distance.

9. The method of claim 6, further comprising choosing said criterion to comprise: two consecutive image formation time, $t=t_{f1}$ and $t=t_{f2}$ satisfy $$|t_{f2}-t_{f1}| \geq \Delta t(\text{thr}),$$

where $\Delta t(\text{thr})$ is a selected threshold separation time.

10. The method of claim 6, further comprising choosing said criterion to comprise:

providing a numerical measure $ID(t_1; t_2)$ of differences in an image formed by said mobile device at times $t=t_1$ and $t=t_2 (>t_1)$; and the measure ID at two consecutive image formation times, $t=t_{f1}$ and $t=t_{f2}$ satisfies $$ID(t_{f1}; t_{f2}) \geq ID(\text{thr}),$$

where $\Delta ID(\text{thr})$ is a selected image difference threshold value.

11. The method of claim 1, further comprising choosing at least one of said sets of coordinate values, $(x1,y1,z1)$, $(x2,y2,z2)$, $(x3,y3,z3)$ and $(x4,y4,z4)$, to produce a magnitude of an inverse of a determinant, $1/|\det(M)|$, of said matrix M having a small positive value.

* * * * *